May 27, 1941. C. L. FITZGERALD Plant Pat. 468
ROSE
Filed Dec. 7, 1940
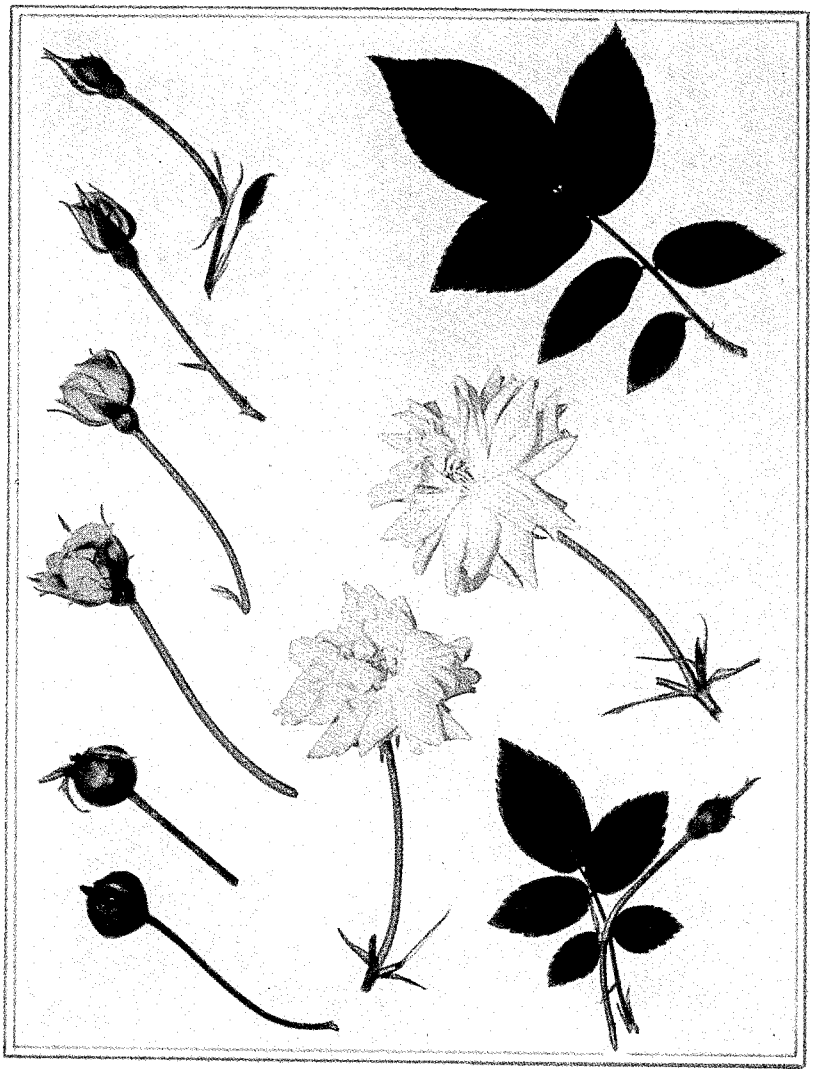
CHARLES L. FITZGERALD,
BY Alfred W. Knight
ATTORNEY.

Patented May 27, 1941

Plant Pat. 468

UNITED STATES PATENT OFFICE

468

ROSE

Charles L. Fitzgerald, Hawthorne, Calif.

Application December 7, 1940, Serial No. 369,087

1 Claim. (Cl. 47—61)

My invention relates to improvements in "baby" roses, and pertains particularly to a deep pink rose of a size comparable to the well-known Cecil Brunner, but differing therefrom in color of flower and in certain other particularities. The variety of rose of the present invention is the result of hybridization and cross-hybridization from hybrid highly colored roses of my own development, and the Cecil Brunner. These hybrid highly colored roses were developed between 1911 and 1926, the small well colored roses from these plants were cross-bred with a bush Cecil Brunner as a mother. The well developed crosses from this hybridization were then bred and cross-bred with a bush Cecil Brunner, with the realization of the present variety in 1937.

The parent seedling of the present variety was grown under glass until six inches tall, was then transplanted and has since been growing outside, at a location near the city of Los Angeles, California, within a few miles of the Pacific Ocean and within the so-called "fog-belt." This variety has been found to reproduce asexually true to type and character.

The accompanying color plate shows the development of a bloom, from an immature bud through the full bloom stage to the final mature fruit, together with two leaves in different stages of development.

The following is a detailed description of my new rose. Where references are made herein to colors, by plate and number, it will be understood that the reference is to the corresponding plate and color patch of "A Dictionary of Color" (Maerz and Paul, McGraw-Hill, 1930). Where a color name is given in parentheses, following the plate and number, that name is the one ascribed by Maerz and Paul as being the most common or prevalent name for that color.

The present variety of rose is a bush or upright rose, a good grower, and an excellent bloomer. The bush will carry blooms or buds constantly, from spring to late fall or early winter. The plant is resistant to mildew, rust and black spot.

*The plant*

The foliage is medium in quantity. The new wood is colored Plate 7, L—7 (Maroon), while the old wood is colored Plate 23, L—4 (Quaker Green). The leaves are unequally pinnate, glossy and quite firm in texture; the mature leaf usually comprises a branch of five to seven leaflets, carried on a petiole about one and three-quarters to two and one-quarter inches in length. The leaflets are medium broad with respect to their length, the mature terminal leaflet being on an average of one and three-quarters inches to two inches long by slightly less than one inch broad. The terminal leaflet is usually more pronouncedly apiculate than are the other leaflets on the same leaf. The leaf color is approximately that of Plate 23, J—8 (Mt. Vernon Green) on old wood, and Plate 24, L—1 (Brewster Green++) on new wood. The leaf, when mature, measures from three and three-quarters to four inches long and about three inches wide as measured from tip-to-tip on the outermost opposed leaflets. The proximal end portion of the terminal leaflet often overlaps the distal edge portions of the outermost pair of opposed leaflets to some extent, owing to the relatively short length (three-eighths of an inch or so) of the petiole between the base of the terminal leaflet and the attachment of such outermost opposed leaflets. The petiole carries two adnate stipules and a few very small and fine briars are occasionally found on the under side of the petiole. The edges of the leaflets are finely notched, with an irregular spacing varying from one to three thirty-seconds of an inch.

The canes are fairly free from thorns, some canes having scarcely any thorns and others carrying some occurring singly but sometimes in pairs, about three to four inches apart along the length. The new wood at the bloom has no thorns at all, but as the wood gets older fine prickles develop, some of which mature as thorns which reach a length of three-eighths of an inch in some instances. The color of the new thorn is approximately that of Plate 7, L—7 (Maroon).

*The flower*

The buds when immature are quite pointed but ovoid. When the bud is about one-half open the bud becomes distinctly ovoid. Just prior to opening, the bud is about eleven-sixteenths of an inch long from tip of the sepals to the juncture of calyx and peduncle, and about one-quarter of an inch in diameter. The calyx is approximately Plate 18, J—7 (Spring Green), shading down to Plate 13, L—12 (Gold Pheasant). The peduncle is approximately that of Plate 22, L—2 (Palm). The sepals vary a little in color from that of the base of the calyx, being approximately that of Plate 18, L—5 on the inside and Plate 22, L—3 (Box Green) on the outside, shading down to Plate 13, L—12 (Gold Pheasant). The flower petals when first opened are approximately Plate 2, I—6, with a deeper (magenta) shading in parts. The main color of the petal shades down to Plate 9, K—5 (Apricot Yellow) at the base.

The bloom opens full, the petals being arranged loosely in five rows, and curling back at outer edges to give the appearance of long pointed cones. The permanence is good; the petals drop free when full blown. The color of the petals when the bloom is full open approximates that of Plate 52, K—2, fading down to a light pinkish cream and then developing into a faint Popcorn color at the base; this color is best illustrated at Plate 9, J—3. Just before dropping off, the petals fade to a pale pink, best illustrated at Plate 2, C—4. The bloom has a slight but definite "Tea" fragrance. As in most highly colored roses, the roses are somewhat darker in color as the days get cooler and shorter with the approach of late fall. Furthermore, the above colors were determined upon flowers growing on bushes planted outside, late in August, and if the buds are picked for a bouquet and kept inside, the colors remain a deeper shade.

*Genital organs*

The anthers and stamens on the open rose are partly concealed by overcurled inside petals. The color of the stamens is substantially that of Plate 2, L—10 (Spark) and the color of the stamen filaments is that of plate 9, J—8 (Genista); the pollen is colored as in Plate 10, L—7 (Golden Yellow); the color of the styles is that of Plate 5, K—5 (Hollywood); the tips of the stigmas are the color of Plate 10, J—1 (Sulphur Yellow), while the filaments thereof are the color of Plate 10, J—3; the ovaries are the color of Plate 11, B—1 (New Silver).

*Fruit*

The fruit is sterile unless hand fertilized. When mature the fruit is practically spherical, with a coarsely rugose surface, approximately one-half inch in diameter. The color of the fruit is that of Plate 7, L—7 (Maroon), while the dried sepals are somewhat lighter in color, approximating Plate 7, J—7 (Roan).

I claim:

The variety of fragrant hybrid bush baby rose herein shown and described, characterised particularly in its deep pink coloring, its faint but distinct "Tea" fragrance, its freedom from thorns on the new wood, and its resistance to disease, particularly mildew, rust and black spot.

CHARLES L. FITZGERALD.